United States Patent [19]  
Jensen et al.

[11] 4,293,536  
[45] Oct. 6, 1981

[54] ESTROPHILIN DETECTION

[75] Inventors: Elwood V. Jensen; Verne D. Hospelhorn, both of Chicago, Ill.

[73] Assignee: University Patents, Inc., Norwalk, Conn.

[21] Appl. No.: 37,631

[22] Filed: May 10, 1979

[51] Int. Cl.³ .................... G01N 33/48; G01T 1/00; A61K 43/00; G01N 23/06
[52] U.S. Cl. ............................. 424/1; 23/230 B; 424/1.5; 424/12
[58] Field of Search ................ 424/1, 1.5, 9, 12; 23/230 B

[56] References Cited  
PUBLICATIONS

Truong et al., Chem. Abstracts, vol. 83, No. 11, Sep. 15, 1975, Astract #93229h.
Fishman et al., J. Clin. Endocrinol, Metab., 39: 603–606 (1974).
Korenman et al., J. Clin. Endocrinol. Metab., 30: 639–645 (1970).

*Primary Examiner*—Deborah L. Kyle  
*Assistant Examiner*—Christine M. Nucker  
*Attorney, Agent, or Firm*—Merriam, Marshall & Bicknell

[57] ABSTRACT

Estrogen receptor protein, estrophilin, in a tissue sample is detected and quantified by radiochemical methods involving selective binding of the protein to controlled pore glass beads. Also disclosed are methods for selectively removing undesirable degradation products from radiochemically labelled non-polar steroid reagents, especially estradiol.

14 Claims, No Drawings

ESTROPHILIN DETECTION

The invention described herein was made in the course of work under a grant or award from the Department of Health, Education and Welfare.

The present invention relates generally to quantitative determinations performed on biological materials, and more specifically to novel materials and in vitro methods for detection and quantification of estrogen receptor protein as well as to methods for treatment of radiochemical reagents to enhance their usefulness in biological assays.

It is generally recognized that specific estrogen-binding proteins, called "estrogen receptors" or, generically "estrophilin" are responsible for the uptake of estrogenic hormones by certain tissues. The hormones are believed to interact with extranuclear estrophilin present in hormone-dependent or "target" cells, with the "activated" estrogen-receptor complex so formed being translocated to the cell nucleus where it binds to the chromatin and in some way enhances the ability of the nucleus to synthesize certain types of RNA.

It has been determined that certain tissues, notably certain human breast cancer tissues, are estrogenic hormone "dependent" in the sense that systemic deprivation of supportive estrogen will result in regression of tissue growth and cell proliferation. As one example of this dependence, bilateral adrenalectomy can effect striking remisssion of advanced breast cancer in post-menopausal women and similar remissions are observed after hypophysectomy. Estrogen deprivation by surgical ablation of tissue responsible for estrogen production and/or endocrine additive therapy afford the most effective treatments presently available for advanced breast cancer. Unfortunately, less than one-half of the premenopausal patients and even a smaller fraction of postmenopausal patients respond to this type of therapy—indicating that breast cancer tissue is not always of the cellular type which is estrogenic hormone dependent. Consequently, it is significant to the prognosis and treatment of human breast cancer to be able to ascertain whether excised tumor tissue of a breast cancer patient is comprised predominantly of estrogen dependent cell types. On the basis of such information, a reasonable ablation response prediction may be made. Surgical removal of estrogen producing glands for the purpose of estrogen deprivation may be restricted to those patients most likely to be helped by the procedure. Correlatively, other breast cancer patients can be spared the trauma of essentially useless surgery and may be placed immediately into alternative therapeutic programs such as radiation or chemotherapy.

Heretofore, the presence of estrogen-dependent tissue in mammary tumor samples has principally been determined by quantitative detection of estrophilin in the sample through radiochemical assay. According to one such procedure, radioactive (e.g., tritiated) estradiol is added to the cytosol—or supernatant fraction—of a homogenized tissue sample, and the tritiated estradiol reversibly combines with any estradiol receptor protein present in the cytosol. The specimen is then subjected to low-salt, sucrose density gradient ultracentrifugation and the proteinestradiol complex, being a large molecule, sediments with a characteristic velocity. A radioactive count can be used to quantify the complex. [See, e.g., Jensen, et al., *J. Steroid Biochem.*, 7, 911–917 (1976); see also, Jensen, et al., "Estrogen Receptors and Breast Cancer Response to Adrenalectomy", *National Cancer Institute Monograph*, 34, 55–77 (1971)]. This procedure is carried out in the presence and in the absence of an inhibitor of the desired specific binding in order to identify and exclude any binding that is non-specific. The above analytical technique requires use of rather sophisticated, costly and uncommon ultracentrifugation apparatus, the operation of which requires a high degree of skill on the part of the laboratory worker. Other methods employed for receptor assays have similar limitations. [See, e.g., Korenman et al., *J. Clin. Endocrinol. & Metab.*, 30, 639–645 (1970)].

Among the other assay techniques available in the art are those of Clark, et al., *Biochim. Biophys. Acta*, 192, pp. 508–515 (1969), as modified by Notides, *Endocrinology*, 87, pp. 987–992 (1970). Briefly put, these publications propose that, in the presence of excess quantities of labelled estradiol, estrogen receptor in a sample will selectively and quantitatively bind to charged particles such as cellular nuclear material pellets, ground glass or silica, if the mixture of these materials is incubated at relatively high temperatures (about 25° C.) for 30 to 45 minutes. The presence of estradiol and extended exposure to incubation temperatures is disclosed as being necessary to transform the so-called inactive form of receptor to the activated form which will bind to the pellets in much the same manner as the activated form binds to materials in the cell nucleus. It is unfortunately the case that such heat treatment of estrophilin will most frequently bring about degradative effects on the protein, rendering the assay inaccurate. Further, an additional source of inaccuracy may be found in the incomplete "conversion" of receptor from inactive to activated form. Finally, use of large excesses of labelled estradiol invariably gives rise to difficulties in removing unreacted labelled reagent, which, in turn adversely affect the accuracy of the assay.

Additionally pertinent to the background of the present invention is the fact that prior methods for quantifying receptor protein in breast cancer tissue measure only the protein not occupied (i.e., "unbound") by endogenous hormone. In premenopausal women or in patients who have undergone treatment with long acting estrogens, the level of unoccupied receptor found in the cytosol (cytoplasmic tissue fraction) may not reflect the true receptor content of the tumor because a significant portion of the protein may have been translocated to the cell nucleus complexed (i.e., "bound") with nonradioactive hormone. While methods have been developed for the exchange of estrogen bound to receptor protein in the nucleus [e.g., Anderson, et al., *J. Biochem.*, 126, pp. 561–567 (1972); and Zava, et al., *Biochemistry*, 15, pp. 4292–4297 (1976)], these procedures also require warming of receptor complexes to temperatures at which decomposition of the protein may occur.

There exists, therefore, an ongoing substantial need for procedures permitting the rapid, accurate determination of bound and unbound estrogen receptor protein in nuclear and cytoplasmic tissue samples. Such procedures would ideally involve use of relatively simple analytical apparatus, would not require use of large excesses of radiochemical reagents, would not rely on conversion of protein to activated binding form, would not require special handling to avoid non-specific binding reactions, and, most significantly, would not involve the treatment of receptor protein under relatively high temperature conditions which promote its destruction.

A further widespread problem in the art exists in the use of radioisotopically labelled non-polar steroid substances such as tritiated estradiol, labelled progesterone analogues (e.g., that commonly referred to as "R5020"), and labelled glucocorticoid analogues such as dexamethasone as reagents in quantification of, e.g., steroid receptor proteins. It is most frequently the case that these reagents degrade upon standing for even short periods to form relatively more highly polar products. The presence of these products in assay reagents will in some instances bind more than the expected or desired quantity of radioactive component to the material to be quantified. In other instances the products become complexed or otherwise entrained in the sample in a manner that renders removal by standard rinsing techniques difficult, if not impossible. This involvement of degradative impurities in the analytical system, of course, substantially diminishes the accuracy of the radiochemical assays. Prior attempts to remove degradation products from such reagents have usually involved paper chromatography and have not been uniformly successful.

There therefore also exists a substantial need in the art for simple methods by which radioactively labelled hormonal reagents may be purified of undesirable degradation products prior to their use in biochemical assays.

BRIEF SUMMARY

The present invention provides novel methods and materials for rapid quantification of bound and unbound estrophilin in both nuclear and cytoplasmic fractions of tissue samples. The invention has its origin, in part, in the discovery of the capacity of microporous beads of a defined pore size to bind estrogen receptor protein: selectively from among other tissue sample components; under low temperature conditions which are not conducive to receptor protein degradation; in the absence of estradiol in labelled or unlabelled form; irrespective of the estrogen bound or unbound state of the receptor; irreversibly under ordinary assay conditions; and in a manner not interfering with the continued capacity of the receptor protein to complex reversibly with estradiol, including tritiated estradiol reagents. The invention has as its basis, therefore, the contacting of a tissue sample with a plurality of such porous beads to effect the formation of a stable product comprising the beads having adhered to surface portions thereof estrogen receptor protein in estrogen bound or unbound state.

According to one aspect of the invention, unbound ("inactive") estrophilin in a tissue sample is selectively removed and bound onto controlled pore glass beads having pore diameters of from about 400 to about 1200 Å (and preferably about 500 Å) and provided in a mesh size of from about 100 to 400. The selective extraction is carried out at non-degradative, low temperatures of from about 1° to 6° C. (preferably about 2° to 5° C.) and may be preceded or followed by complexing of the receptor with a relatively small excess of labelled estradiol. The labelled material is then eluted with a suitable solvent and quantified to provide an assay for the estrophilin in the sample.

According to another aspect of the invention, bound estrophilin in a tissue sample is measured by an exchange process wherein the sample is first extracted with porous glass beads as described above. Once again, the procedure is carried out at low temperatures and results in quantitative removal of all the receptor protein in the sample. Quantification of the protein is then accomplished by an exchange process wherein a heavy metal ion (preferably supplied as a soluble monovalent metal salt) dissociates the estrogen/estrophilin complex, but leaves the receptor adhered to the glass beads. The heavy metal is, in turn, removed from the system by treatment with a sulfhydryl group-containing compound reactive with the metal to form a soluble heavy metal mercaptide, thereby freeing the receptor protein. After removal of the metal, the receptor is then complexed with labelled estradiol and quantified by elution and counting of the labelled material.

In still another aspect, the invention provides for quantification of total bound and unbound estrophilin by means of pretreatment of a tissue sample containing the same with estradiol. The total quantity of estradiol/-receptor complex is then determined by the exchange procedure described above.

In another aspect, the present invention provides methods for removal of undesirable degradation products from labelled non-polar steroid reagents wherein the reagent is contacted with porous glass beads of the type described above.

Other aspects and advantages of the present invention will become apparent upon consideration of the following detailed description.

DETAILED DESCRIPTION

The following description includes, at times, the use of certain abbreviations: "E" shall mean estradiol; "E*" shall mean tritiated estradiol; "R" shall mean estrogen receptor protein (estrophilin); "ER" and "E*R" shall respectively designate a complex association of estrophilin with estradiol or tritiated estradiol; "CPG" shall mean a controlled pore glass beads; associations of controlled pore glass beads with other substances shall be designated "CPG--R", "CPG--E*R" and the like; heavy metal atoms shall be represented by "M"; and sulfhydryl group-containing materials shall be represented as "(SH)".

The reagents and materials employed in certain of the illustrative examples include the following. [6,7-$^3$H] Estradiol-17$\beta$ (57 Ci/mmol) was obtained from New England Nuclear Co. and, unless otherwise noted, E* represents this 6,7-tritiated estradiol. Controlled pore glass beads were obtained from Electro-Nucleonics, Inc. (Fairfield, New Jersey). Unless otherwise noted, CPG indicates beads of the following description: mesh size, 120–200; mean pore diameter, 493 Å; pore dist. (±%), 7.7; pore volume (cc/g), 1.25; and surface area (M$^2$/g), 52.4. Glass microfibre paper was obtained from Whatman, Ltd. Buffers incorporating Tris (T) and potassium nitrate or chloride (K) are designated according to the millimolarity of their components, e.g., $T_{10}K_{400}$=10 mM Tris/400 mM KNO$_3$ (or KCl). pH adjustments of all buffers were made with the appropriate acid of the salt used.

The following examples illustrate practice of the invention and more specifically relate to: procedures for determination of unbound receptor protein; procedures for detection of bound receptor protein; procedures for detection of total (bound and unbound) receptor protein; a comparison of analysis according to the invention and prior art methods involving sucrose gradient and dextrancoated charcoal analytical systems; and purification of a labelled estradiol reagent.

EXAMPLE 1

A suitable column for practice of the present invention may be prepared through use, e.g., of a vertically-supported 2.5 ml glass syringe. A small disc of glass microfibre paper is placed in the bottom of the syringe and wetted with a drop of $T_{10}K_{400}$ buffer solution, pH 8.4. Onto the disc is pipetted 0.4 ml of a CPG/buffer suspension prepared by mixing, 1:1 v/v, CPG beads in $T_{10}$ buffer (pH 7.4 and including 1.0 mM $NaN_3$) and deaerating. Drainage of the buffer results in a bed volume of CPG beads of 0.2 ml. Another wetted disc is pressed down on top of the beads. The syringe tip is suitably fitted with, e.g., a 16 gauge needle having a length of about 2.5 cm.

In analysis for unbound estrophilin, tissue samples are prepared as follows: Tissue to be examined is homogenized in 4:1 (v/w) buffer of any suitable type (e.g., $T_{10}$ or $T_{10}K_{10}$ at pH 7.4). The homogenate is centrifuged at 250,000 × g for one-half hour and the supernatant ("cytosol") is collected for testing. Preparation of nuclear tissue extracts for testing involves further treatment of the pellet obtained in the above-noted centrifugation process. The pellet is extracted with 4:1 (v/w, based on original tissue net weight) $T_{10}K_{400}$, pH 8.4. A short (e.g., 15 second) homogenization and 15 minute extraction followed by centrifugation at 250,000 × g for one-half hour gives the supernatant fluid which is the nuclear extract. If E* is to be added to a cytosol sample prior to binding of the receptor protein to the column, the following procedure is carried out. Two hundred fifty microliters of cytosol is made 20 nM in E* and allowed to stand for at least one hour at a low temperature of 2°–5° C. Another sample of the same cytosol is made 20 nM in E* and 4 μM in E (i.e., a 200-fold excess of "cold" estradiol) under the same conditions.

The following procedures are carried out in the cold (2° C. to 5° C.). Two CPG packed columns are employed for each determination. Each column is washed with 2 ml of $T_{10}K_{400}$ buffer, pH 8.4. To one column is added 0.2 ml of the sample containing only the E* as prepared above, and to the other column is added 0.2 ml of the sample containing E* and a 200-fold excess of "cold" E. Each column is washed twice with 0.3 ml aliquots of $T_{10}K_{400}$ buffer, pH 8.4, and then with 20 ml of the same buffer. After washing, the columns may be removed from the cold and are allowed to stand at room temperature for 15–20 minutes. Thereafter the columns are eluted with 2 ml portions of absolute ethanol or other agent suitable for disrupting the complex of receptor and estradiol. The alcohol eluant is then counted, with the ethanol reagent noted to cause about 25% quenching of the count.

The principle reactions in the above procedure may be represented as follows:

E*+R→E*R  (1)

E*R+CPG→CPG-E*R  (2)

CPG-E*R $\xrightarrow{alcohol}$ CPG-R+E*  (3)

A modification of the above procedure wherein the receptor protein is not pre-treated with labelled estradiol, but is instead first adsorbed on the controlled-pore glass beads and then complexed with the radiochemical, will provide equally accurate results.

EXAMPLE 2

Controlled pore glass bead packed columns are prepared as in Example 1. Tissue samples (e.g., nuclear extracts) upon which a determination of bound receptor protein is to be conducted are prepared as noted above. The following reagent solutions are prepared:

A stock aqueous solution of 0.125 M silver nitrate is diluted to $1.25 \times 10^{-3}$ M in $T_{10}$ buffer (pH 8.4) immediately prior to use. A "standardized" solution of from $1 \times 10^{-9}$ to $5 \times 10^{-9}$ M E* and 0.01 M 1,4-dithiothreitol (DTT) is made up in $T_{10}K_{400}$ buffer, pH 8.4. A similar solution containing the same quantity of E* and about a 200-fold excess of E is also prepared.

The following procedures are carried out in the cold. Three CPG packed columns are employed. To columns 2 and 3 is added 200 μl of the tissue extract, followed by two 0.3 ml washes with $T_{10}K_{400}$ buffer, pH 8.4, and then a 10 ml wash with the same buffer through all columns. To columns 2 and 3 is added 0.8 ml of the silver nitrate solution. All columns are washed with 20 ml of $T_{10}K_{400}$ buffer, pH 8.4. At this stage, appropriate measures are taken to facilitate slow passage of labelled reagents through the columns. A desired flow rate of 0.6 to 0.7 ml per 20 minutes may be obtained by replacing the needle with an 11 cm. segment of polyethylene tubing (I.D. 0.011 inches) and providing the tubing with a 360° loop of a size which will result in a total vertical directional length of about 6.5 cm for the attached tubing.

To columns 1 and 2 is added 2 ml of the standardized E*/DTT solution in three portions comprising 0.6, 0.7 and 0.7 ml. To column 3 is added the E*/DTT solution containing excess E. After passage of the steroid through the columns, the tubing is removed and all columns are washed with two 0.8 ml portions of $T_{10}K_{400}$ buffer and then a 20 ml portion of buffer.

Columns are eluted with alcohol as in Example 1 and a count of the alcohol eluant from column 2 (minus the "background" count of column 3) provides the bound receptor protein determination value. Counts retained on column 1 are due to retention of the steroid in the bead bed and should be essentially the same as the counts on column 3.

The principle reactions in above procedures may be represented as follows:

ER+CPG→CPG-ER  (1)

CPG-ER+M→CPG-RM  (2)

CPG-RM+(SH)/E*→CPG-E*R  (3)

CPG-E*R $\xrightarrow{alcohol}$ CPG-R+E*  (4)

While the above procedure directs addition of the sulfhydryl group-containing substance (e.g., DTT) simultaneously with E*, this addition may separately precede the E* addition.

If there is unbound receptor present in the tissue extract, the above procedure appears to be inappropriate for the determination of total receptor protein (e.g., by subtracting the column 3 count from that of column 2) owing to undetermined effects of the heavy metal on the receptor when in its unbound form.

EXAMPLE 3

A determination of total bound and unbound receptor protein content of a given tissue sample may be conducted by practice of the procedures of Example 2 after the initial step of complexing unbound receptor in the sample with unlabelled estradiol. This step serves to place all receptor protein in the sample into complex association with estradiol to avoid the heavy metal treatment effects noted above and can be accomplished simply by passing E through all but column 1 in the Example 2 procedure, immediately after the test samples are added to the CPG beads.

EXAMPLE 4

In order to verify the accuracy and effectiveness of the procedures of Example 1, a tissue sample comprising immature rat uterus cytosol was assayed for unbound receptor by the Example 1 method as well as by the sucrose density gradient method [Toft, et al., *P.N.A.S.*, 55, pp. 1574-1581 (1966)] and the Scatchard procedure [Scatchard, *Ann. N.Y. Acad. Sci.*, 51, pp. 660-672 (1949)], dextran coated charcoal methodology [Korenman, et al., *J. Clin. Endocrin.*, 30, pp. 639-645 (1970)]. Values for receptor concentration determined by the CPG bead method and sucrose density gradient methods were substantially identical ($9.5 \times 10^{-10}$M and $9.6 \times 10^{-10}$M, respectively) while the value obtained by the dextran-coated charcoal method was substantially lower ($6.0 \times 10^{-10}$M). The diminished value for the coated charcoal assay may be attributed to adsorption of receptor protein on the charcoal or removal of estradiol from receptor by the charcoal, or both, during the required incubation process.

EXAMPLE 5

Solutions of E* or other labelled non-polar steroid may be cleansed of undesired degradation products by simple passage through a column of CPG beads prior to use in the assays set out in Examples 1 through 3. Flow rates through the CPG bead packed columns of from 0.03 to 0.05 ml/minute are appropriate. Practice of this procedure immediately prior to practice of the methods of Example 2, for example, will result in substantially no residual count in the CPG bead bed of column 1.

It will be apparent to those skilled in the art that numerous modifications and variations may be made in practice of the invention illustrated in the above examples.

As specifically noted above, CPG beads having a pore diameter of about 500 Å are preferred but good results are expected to attend use of beads having a diameter in the range of 400 to 1200 Å. Similarly, selection of a CPG bead mesh size of 120-200 is preferred but beads of a mesh size of 100 to 400 should prove acceptable.

While Example 2 illustrates the use of silver nitrate solutions as a donor of heavy metal ions in the hormone exchange procedure, it will be understood that a variety of heavy metal ion sources may be employed. Necessary characteristics of suitable metallic compounds include solubility in water and general compatability with solvent systems employed in the assay. Along with silver nitrate, soluble heavy metal ion sources include not only other inorganic salts providing monovalent ions but organometallic compounds such as p-chloromercuribenzoate which effectively supplies a monovalent mercury ion in water solution. Generally unsuitable are insoluble heavy metal salts such as silver chloride. In this respect it should be noted that some departure from conventional sample and buffer preparations may need to be made to avoid formation of insoluble metal salts during the exchange procedures. Tissue sample preparation using potassium chloride should be avoided owing to the presence of chloride ions.

Sulfhydryl group-containing reagents other than dithiothreitol may be employed in practice of the invention provided they suitably react with the selected heavy metal to form soluble salts in the exchange process. One such reagent is dithioerythritol.

While the above examples relate to use of a ditritiated estradiol reagent, it will be apparent that tetra- and hexa-tritiated reagents are also useful, as would be estradiol labelled with substances other than tritium.

What is claimed is:

1. A method for determining the quantity of estrophilin in a tissue sample, said method comprising:
   (1) contacting said sample with a plurality of porous glass beads having a pore diameter of from about 400 to about 1200 Å to selectively adhere said estrophilin to the pore surfaces of said beads;
   (2) contacting estrophilin in said sample with radioactively labelled estradiol to form a stable complex association of estrophilin bound to estradiol; and
   (3) selectively removing laballed estradiol from complex association with estrophilin and measuring the quantity of labelled estradiol so removed.

2. The method of claim 1 wherein the step (1) of contacting said sample with said beads is carried out at a temperature of from about 1° to about 6° C.

3. The method of claim 1 wherein the step (2) of forming a complex association of labelled estradiol bound to estrophilin precedes the step (1) of selectively adhering estrophilin to pore surfaces of the glass beads.

4. The method of claim 1 wherein the step (2) of forming a complex association of labelled estradiol bound to estrophilin follows the step (1) of selectively adhering estrophilin to pore surfaces of said glass beads.

5. The method of claim 4 wherein the step (2) of forming a complex association of labelled estradiol bound to estrophilin comprises the following steps:
   (a) selectively dissociating non-labelled estradiol bound in complex association to estrophilin with a heavy metal ion by treatment with a water soluble source of heavy metal ions;
   (b) selectively displacing heavy metal ion bound in complex association with esrophilin by treatment with a water soluble sulfhydryl group-containing reagent capable of forming a soluble heavy metal salt with said metal ion; and,
   (c) contacting estrophilin adhered to said glass beads with radioactively labelled estrogen.

6. The method of claim 5 wherein said water soluble source of heavy metal ion is silver nitrate.

7. The method of claim 5 wherein said sulfhydryl group containing reagent is dithiothreitol.

8. The method of claim 5 wherein steps (b) and (c) are simultaneously practiced subsequent to practice of step (a).

9. The method of claim 1 wherein said glass beads have a pore diameter of about 500 Å.

10. The method of claim 1 wherein said step (3) of removing labelled estradiol from complex association with estrophilin comprises the step of washing with ethanol.

11. The method of claim 1 wherein said radioactively labelled estradiol is [6,7-$^3$H]-estradiol-17$\beta$.

12. A plurality of porous glass beads having a pore diameter of from about 400 to 1200 Å and having estrophilin adhered to pore surfaces thereof.

13. A method for removing degradation products from a solution of radioactively labelled non-polar steroid, said method comprising contacting said solution with a plurality of porous glass beads having a pore diameter of from about 400 to 1200 Å to selectively adhere said degradation products to pore surfaces of said beads.

14. The process of claim 13 wherein said steroid is tritiated estradiol.

* * * * *